(12) United States Patent
Grodzki (10) Patent No.: US 10,539,638 B2
(45) Date of Patent: Jan. 21, 2020

(54) METHOD AND MAGNETIC RESONANCE APPARATUS FOR OPTIMIZATION OF A SEQUENCE OF MULTIPLE SCAN PROTOCOLS FOR AT LEAST ONE MAGNETIC RESONANCE EXAMINATION

(71) Applicant: Siemens Healthcare GmbH, Erlangen (DE)

(72) Inventor: David Grodzki, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 301 days.

(21) Appl. No.: 15/214,657

(22) Filed: Jul. 20, 2016

(65) Prior Publication Data

US 2017/0023655 A1  Jan. 26, 2017

(30) Foreign Application Priority Data

Jul. 20, 2015 (DE) .......................... 10 2015 213 595

(51) Int. Cl.
*G01R 33/54* (2006.01)
*G01R 33/38* (2006.01)
*G16H 40/63* (2018.01)
*G01R 33/385* (2006.01)
*G01R 33/28* (2006.01)

(52) U.S. Cl.
CPC ....... *G01R 33/3804* (2013.01); *G01R 33/543* (2013.01); *G16H 40/63* (2018.01); *G01R 33/288* (2013.01); *G01R 33/3856* (2013.01)

(58) Field of Classification Search
CPC ....................... G01R 33/3804; G01R 33/543

USPC ......................................................... 324/309
See application file for complete search history.

(56) References Cited

U.S. PATENT DOCUMENTS

| | | | |
|---|---|---|---|
| 5,512,825 | A | 4/1996 | Atalar et al. |
| 7,443,166 | B2 | 10/2008 | Heid |
| 8,035,378 | B2 | 10/2011 | Schnell et al. |
| 8,502,532 | B2 | 8/2013 | Assmann et al. |

(Continued)

FOREIGN PATENT DOCUMENTS

| | | |
|---|---|---|
| CN | 1654009 A | 8/2005 |
| CN | 101458313 A | 6/2009 |

(Continued)

OTHER PUBLICATIONS

Grodzki et al., "Improved Utilization of Gradient Power," Siemens AG Publication, Mar. 30, 2015.

(Continued)

*Primary Examiner* — Reena Aurora
(74) *Attorney, Agent, or Firm* — Schiff Hardin LLP (57) ABSTRACT

In a method for the optimization of multiple scan protocols for at least one magnetic resonance examination is performed by a magnetic resonance apparatus, patient data for at least one patient are recorded that includes the selection of two or more different measurements, each including at least one scan protocol, which includes at least one magnetic resonance examination. An optimized sequence of the multiple scan protocols for the two or more different measurements for the at least one magnetic resonance examination is determined by a protocol optimization computer. The optimized sequence of the multiple protocols is presented at a display monitor.

13 Claims, 2 Drawing Sheets

(56) References Cited

U.S. PATENT DOCUMENTS

| | | |
|---|---|---|
| 8,892,183 B2 | 11/2014 | Gericke et al. |
| 9,684,048 B2 | 6/2017 | Grodzki et al. |
| 2005/0154292 A1* | 7/2005 | Tank ................. A61B 5/055 600/410 |
| 2009/0146660 A1 | 6/2009 | Schnell et al. |
| 2009/0182219 A1 | 7/2009 | Gericke et al. |
| 2009/0315561 A1 | 12/2009 | Assmann et al. |
| 2011/0043204 A1 | 2/2011 | Bielmeier et al. |
| 2013/0090776 A1 | 4/2013 | Feiweier |
| 2013/0181708 A1 | 7/2013 | Biber et al. |
| 2014/0232396 A1 | 8/2014 | Grodzki et al. |
| 2016/0239961 A1* | 8/2016 | Haider ..................... G06F 3/14 |

FOREIGN PATENT DOCUMENTS

| | | |
|---|---|---|
| DE | 102004038619 A1 | 2/2006 |
| DE | 10 2006 034 397 B3 | 12/2007 |
| DE | 10 2008 004 469 A1 | 7/2009 |
| DE | 10 2008 029 897 A1 | 2/2010 |
| DE | 10 2009 038 139 A1 | 2/2011 |
| DE | 10 2013 202 559 B3 | 8/2014 |

OTHER PUBLICATIONS

Grodzki et al., "Preview of heating resulting from a scan," Siemens AG Publication Document (2015).
German Office Action dated Apr. 11, 2016, for Application No. 10 2015 213 595.0.
Chinese Action dated Dec. 25, 2018, for Application No. 2016105696579, and English translation.

* cited by examiner

FIG 1

METHOD AND MAGNETIC RESONANCE APPARATUS FOR OPTIMIZATION OF A SEQUENCE OF MULTIPLE SCAN PROTOCOLS FOR AT LEAST ONE MAGNETIC RESONANCE EXAMINATION

BACKGROUND OF THE INVENTION

Field of the Invention

The present invention concerns a method for the optimization of a sequence of multiple (two or more) scan protocols for at least one magnetic resonance examination by operation of a magnetic resonance apparatus. The present invention also concerns a magnetic resonance apparatus designed to implement such a method.

Description of the Prior Art

In clinical tomography, magnetic resonance imaging is advantageously used due to its ability to show soft tissue with high contrast. Different contrasts can be generated within the image data as a function of imaging sequences, such as a TSE sequence (turbo-spin-echo sequence), GRE sequence (gradient echo sequence) etc., and parameter selection, such as a TE parameter (echo time parameter) and/or a TR parameter (relaxation time parameter) etc., in the scan protocols.

Individual components of a magnetic resonance apparatus, in particular a gradient coil arrangement of the magnetic resonance apparatus, are loaded to different degrees as a function of a selected sequence and/or a selected scan protocol. For example, a diffusion-weighted sequence heats the gradient coils of the magnetic resonance apparatus to a greater degree than a T2-weighted sequence. Therefore, to prevent damage to the magnetic resonance apparatus, it is necessary for individual hardware components of the magnetic resonance apparatus to be protected against overheating.

SUMMARY OF THE INVENTION

An object of the present invention is to facilitate optimum utilization of individual components of the magnetic resonance apparatus during a magnetic resonance examination, and in this context to protect the individual components against overheating.

This object is achieved in accordance with the invention the invention by a method for the optimization of a sequence of multiple scan protocols for at least one magnetic resonance examination, wherein the magnetic resonance examination is performed by a magnetic resonance apparatus the method having the following steps.

Patient data are recorded for at least one patient, wherein the recording of the patient data includes a selection of two or more different measurements, each executed according to at least one scan protocol, which includes at least one magnetic resonance examination.

An optimized sequence of the multiple scan protocols for the two or more different measurements for the at least one magnetic resonance examination, is determined by a protocol optimization computer.

The optimized sequence of the multiple scan protocols is presented at a display monitor of the magnetic resonance apparatus.

In this context, the recording of patient data means the acquisition of patient raw data, such as the entry of the patient raw data and/or the retrieval of the patient raw data from a memory and/or the assignment of the patient data to a magnetic resonance examination, for example a knee examination, etc. In this context, the magnetic resonance examination preferably includes two or more different measurements. The two or more different measurements can include, for example, a diffusion measurement and/or a TOF measurement etc. In this context, the selection of the two or more different measurements can take place at least partially automatically by the data acquisition scanner with reference to a magnetic resonance examination which has been selected and/or assigned to the patient data, such as a magnetic resonance examination with the administration of a contrast agent. Moreover, the recording of the patient data can also include the manual selection of a sequence of the two or more scan protocols, wherein to this end a user, for example a medical operator, is able to define a sequence of the two or more different measurements. In this context, the manual selection takes place by means of a user interface of the magnetic resonance apparatus.

The optimized sequence of the two or more scan protocols of the at least one magnetic resonance examination is preferably identified and/or determined with reference to optimization parameters determined by the protocol optimization computer. The optimized sequence of the two or more scan protocols of the at least one magnetic resonance examination includes parameter settings for the magnetic resonance apparatus providing optimum and/or ideal utilization of individual components of the magnetic resonance apparatus and/or the lowest probability of overloading and/or a fault, in particular overheating, of individual components, in particular the gradient coils of the magnetic resonance apparatus. Preferably, the optimized sequence facilitates the provision of an advantageous parameter range for parameters that can be set by medical operators, such as an echo time parameter (TE parameter) or a relaxation time (TR parameter) etc. As long as a manual sequence of the two or more scan protocols was selected during the recording of the patient, it is possible for the optimized sequence to deviate from the selected sequence.

The protocol optimization computer includes the software and/or computer programs required for the selection of the optimized sequence of the scan protocols. In this context, the protocol optimization computer can be included in a system control computer of the magnetic resonance apparatus or in a computer embodied separately from the system control computer of the magnetic resonance apparatus. The optimized sequence of the two or more scan protocols is preferably determined automatically and/or autonomously by the protocol optimization computer.

The display of the optimized sequence of the two or more scan protocols preferably includes a graphical depiction and/or display of the optimized sequence of the two or more scan protocols for a medical operator. To this end, the display monitor preferably includes a graphical output unit, such as a display screen and/or a touch screen, etc.

The invention facilitates the optimum and/or ideal utilization of individual components, in particular the gradient coil, of the magnetic resonance apparatus, with which it is simultaneously possible to prevent overloading of the individual components of the magnetic resonance apparatus, such as the gradient coils. In this context, it is also possible in a particularly simple way for magnetic resonance examinations, including, for example, magnetic resonance sequences implemented by the actual medical operator, for an optimized sequence of the two or more scan protocols to be determined and/or defined and hence for a time-saving preparation of the magnetic resonance examination to be provided for the medical operator. Moreover, it is advantageously possible for the medical operator to be supported during the planning of the magnetic resonance examination and for a time-saving course of the planning to be facilitated.

It is also suggested that, during the patient-recording phase, a sequence of the two or more scan protocols for the two or more different measurements for the at least one magnetic resonance examination can be selected. The sequence of the two or more scan protocols for the two or more different measurements is preferably selected manually by a user. This enables a user to define a desired and/or preferred sequence of the two or more scan protocols for the two or more different measurements and/or notify a system, in particular the protocol optimization computer.

In a further embodiment of the invention, for the determination of the optimized sequence of the two or more scan protocols for the two or more different measurements for the at least one magnetic resonance examination, at least one instance of overall heating of at least one component of the magnetic resonance apparatus is determined for different sequences of the two or more scan protocols for the two or more different measurements for the at least one magnetic resonance examination by the protocol optimization computer. In this context, expected overall heating means heating of the at least one component that occurs during the entire magnetic resonance examination. The at least one component preferably includes at least one gradient coil of the magnetic resonance apparatus. For example, during the determination of the expected overall heating of the gradient coil of the magnetic resonance apparatus, a maximum allowable gradient strength and/or a slew rate is determined, wherein the maximum allowable gradient strength and/or the slew rate can be determined iteratively and the expected overall heating determined and/or estimated with reference thereto. This enables the provision of an optimized sequence of the two or more scan protocols for the two or more different measurements for the at least one magnetic resonance examination in a particularly simply way. This enables a user to be shown different sequences with different degrees of optimization for the selection.

In a further embodiment of the invention, the optimized sequence of the two or more scan protocols for the two or more different measurements for the at least one magnetic resonance examination is determined with reference to a minimum overall heating of the at least one component of the magnetic resonance apparatus. This also facilitates the advantageous protection of individual components of the magnetic resonance apparatus in particular against unwanted overheating. To achieve a minimum overall heating of the at least one component of the magnetic resonance apparatus, the two or more individual measurements are preferably divided such that, over a period of the at least one magnetic resonance examination, the expected heating is as uniform as possible. For example, individual measurements, with particularly high expected heating, such as a diffusion measurement or a TOF measurement, can be arranged spaced as far apart as possible from one another within the optimized sequence. This advantageously enables the avoidance of an arrangement of two measurements with particularly high expected heating directly one after the other within a flowchart and/or an optimized sequence of the two or more scan protocols and hence the avoidance of overheating and/or overloading of components.

The optimized sequence of the two or more scan protocols for the two or more different measurements for the at least one magnetic resonance examination can be determined as a function of an expected heating of at least one component of the magnetic resonance apparatus for at least one of the two or more different measurements. This facilitates a particularly quick determination of the optimized sequence, since the expected heating of the at least one component of the magnetic resonance apparatus, such as a gradient coil, can be restricted, for example, to measurements including a particularly high setting of a gradient strength. Moreover, this enables the optimized sequence of the scan protocols to be defined as a function of the expected heating of the at least one component for the at least one measurement of the magnetic resonance apparatus. Particularly advantageously, however, the expected heating of the at least one component of the magnetic resonance apparatus is determined for all of the two or more different measurements for the at least one magnetic resonance examination.

In a further embodiment of the invention, the expected heating of at least one component of the magnetic resonance apparatus and/or the expected overall heating of at least one component of the magnetic resonance apparatus are used to determine an available parameter space for the magnetic resonance examination by the protocol optimization computer. In this context, a parameter space means a setting option for different measuring parameters, wherein the setting options for the different measuring parameters can be varied as a function of the sequence of the two or more scan protocols. In this context, the parameters can be set by the operator. The different measuring parameters can include, for example, an echo time (TE) or a relaxation time (TR) etc. This embodiment of the invention is able to achieve advantageous component protection for individual components, in particular the gradient coils, of the magnetic resonance apparatus by an advantageous provision of an advisable parameter space for setting the measuring parameters for the magnetic resonance examination. For example, the adaptation of the available parameter space to the expected heating of the at least one component and/or overall heating of the at least one component enables a range and/or a setting option for the setting of the relaxation time to be restricted. Moreover, it is also conceivable for a heating status of the at least one component, in particular a gradient coil, of the magnetic resonance apparatus also to influence the available parameter space for this magnetic resonance examination before the start of the magnetic resonance examination and the available parameter space for this magnetic resonance examination to be determined with reference to the existing heating of the at least one component.

In addition, it can also be provided that the available parameter space is used to determine the optimized sequence of the two or more scan protocols for the two or more different measurements for the at least one magnetic resonance examination by the protocol optimization computer. This has the effect that an advisable parameter space for the magnetic resonance examination can be provided. The sequence of the two or more scan protocols for the two or more different measurements for the at least one magnetic resonance examination is preferably optimized with reference to both the expected heating of the at least one component and/or the expected overall heating of the at least one component and the available parameter space. This facilitates an advantageous matching of the expected heating to the available parameter space.

In a further embodiment of the invention, the optimized sequence of the two or more scan protocols for the two or more different measurements for the at least one magnetic resonance examination is determined as a function of at least one further magnetic resonance examination. In this context, the two magnetic resonance examinations can be arranged directly one after the other or also spaced apart in a flowchart for the magnetic resonance apparatus. This enables the utilization of the system, in particular the magnetic resonance apparatus, and/or the expected heating for individual measurements advantageously to be taken into account when planning a sequence of the different magnetic resonance examinations and planning a sequence of individual measurements within the magnetic resonance examinations. This advantageously enables individual magnetic resonance examinations advantageously to be matched to one another. For example, two magnetic resonance examinations, both including a knee examination and hence severe loading of the gradient coil, are precluded from being performed directly one after the other, but a further magnetic resonance examination is performed therebetween.

In a further embodiment of the invention, the optimized sequence of the two or more scan protocols for the two or more different measurements for the at least one magnetic resonance examination is determined as a function of a heating status of at least one component of the magnetic resonance apparatus before the start of the at least one magnetic resonance examination. This enables the optimization of the sequence of the scan protocols to be defined dependence on previous magnetic resonance examinations. For example, any remaining residual heat resulting from the preceding magnetic resonance examinations in the at least one component, for example the gradient coil arrangement, of the magnetic resonance apparatus can advantageously be taken into account during the optimization of the sequence.

Alternatively or additionally, the optimized sequence of the two or more scan protocols for the two or more different measurements for the at least one magnetic resonance examination can also be determined as a function of an heating status of at least one component of the magnetic resonance apparatus after the end of the at least one magnetic resonance examination and/or on a subsequent magnetic resonance examination. This enables the optimized sequence to be adapted to an expected heating status of the subsequent magnetic resonance examination and/or an expected utilization status of at least one component of the magnetic resonance apparatus for the subsequent magnetic resonance examination. Moreover, this facilitates an as uniform as possible expected utilization and/or expected heating of at least one component of the magnetic resonance apparatus. The expected utilization and/or the expected heating are preferably determined over a measuring period including a plurality of magnetic resonance examinations that are performed one after the other.

In a further embodiment of the invention, following the display of the optimized sequence of the two or more scan protocols for the two or more different measurements for the at least one magnetic resonance examination, a sequence of the two or more scan protocols is selected. The selection preferably takes place manually by a user via a user interface of the magnetic resonance apparatus. This enables the user to select the sequence of two or more of the scan protocols with reference to different sequences of the two or more scan protocols, wherein the different sequences of the two or more scan protocols also include the optimized sequence. This enables the user to select the sequence of the two or more measuring parameters also with reference to further parameters and/or information, for example when a particularly time-optimized magnetic resonance examination is desired, such as is advantageous with patients with a tendency toward claustrophobia.

For the manual selection of the sequence of the two or more scan protocols for the two or more different measurements for the at least one magnetic resonance examination, at least one item of optimization information is determined by the protocol optimization computer. The at least one item of optimization information advantageously enables the individual sequences of the two or more scan protocols for the two or more different measurements for the at least one magnetic resonance examination to be assessed in particular with respect to optimum utilization and/or with respect to optimum parameter setting. The at least one item of optimization information includes a utilization factor of the magnetic resonance apparatus and/or a value of a deviation from the optimized sequence.

The at least one item of optimization information can be displayed differently as a function of a value for a deviation from the optimized sequence of the two or more scan protocols for the two or more different sequences of the scan protocols. This enables the optimization information to be displayed directly and simply for a user. The user is thereby also able to acquire the optimization information simply and quickly. This also facilitates a time-saving selection of the sequence for the user. Preferably, display as a "traffic light" is selected for the evaluation of the individual sequences. For example, during the selection of the sequence comprising the optimized sequence, the optimization information can be displayed or shown to a user by means of a display region with green illumination. If the selection of the sequence includes a sequence in which the energy-intensive measurements are arranged directly one after the other, this can be displayed or shown to a user by a display region with red illumination. It is also possible to use color gradations to display different pieces of optimization information.

The invention also encompasses a magnetic resonance apparatus designed for the optimization of a sequence of two or more scan protocols for at least one magnetic resonance examination. This magnetic resonance apparatus has a data acquisition scanner with which patient data are recorded for at least one patient, wherein the recording of the patient data includes the selection and execution of two or more different measurements each including at least one scan protocol, which includes at least one magnetic resonance examination. The computer also has a protocol optimization computer configured to determine an optimized sequence of the two or more scan protocols for the two or more different measurements for the at least one magnetic resonance examination. The apparatus also has a display monitor in communication with the protocol optimization computer at which the selected optimized sequence of the two or more scan protocols is displayed.

The invention facilitates the optimum and/or ideal utilization of individual components, in particular the gradient arrangement, of the magnetic resonance apparatus with which overloading of the individual components of the magnetic resonance apparatus, is prevented at the same time. It is also particularly simple for an optimized sequence of the two or more scan protocols to be determined and/or defined for magnetic resonance examinations, which, for example, include magnetic resonance sequences implemented by the medical operators themselves, and hence a time-saving preparation of the magnetic resonance examination to be provided for the medical operator. Moreover, the medical operator can be supported in the planning of the magnetic resonance examination and hence a time-saving course of the planning facilitated.

The advantages of the magnetic resonance apparatus according to the invention substantially correspond to the advantages of the method according to the invention for the optimization of a sequence of two or more scan protocols for at least one magnetic resonance examination that were explained above in detail. Features, advantages or alternative embodiments described above with regard to the method are applicable to the apparatus as The invention also encompasses a non-transitory, computer-readable data storage medium that can be loaded directly into a memory of programmable computer or distributed computer system. The storage medium is encoded with programming instructions that cause the computer or computer system to implement the method according to the invention when the programming instructions are executed.

The program code may require program support, e.g. libraries and auxiliary functions, in order to implement the corresponding embodiments of the method. The program code can include software with a source code, which still needs to be compiled and incorporated, or only has to be interpreted, or an executable software code, which only needs to be loaded into a corresponding computing unit for execution.

DESCRIPTION OF THE PREFERRED EMBODIMENTS

Figure 1:
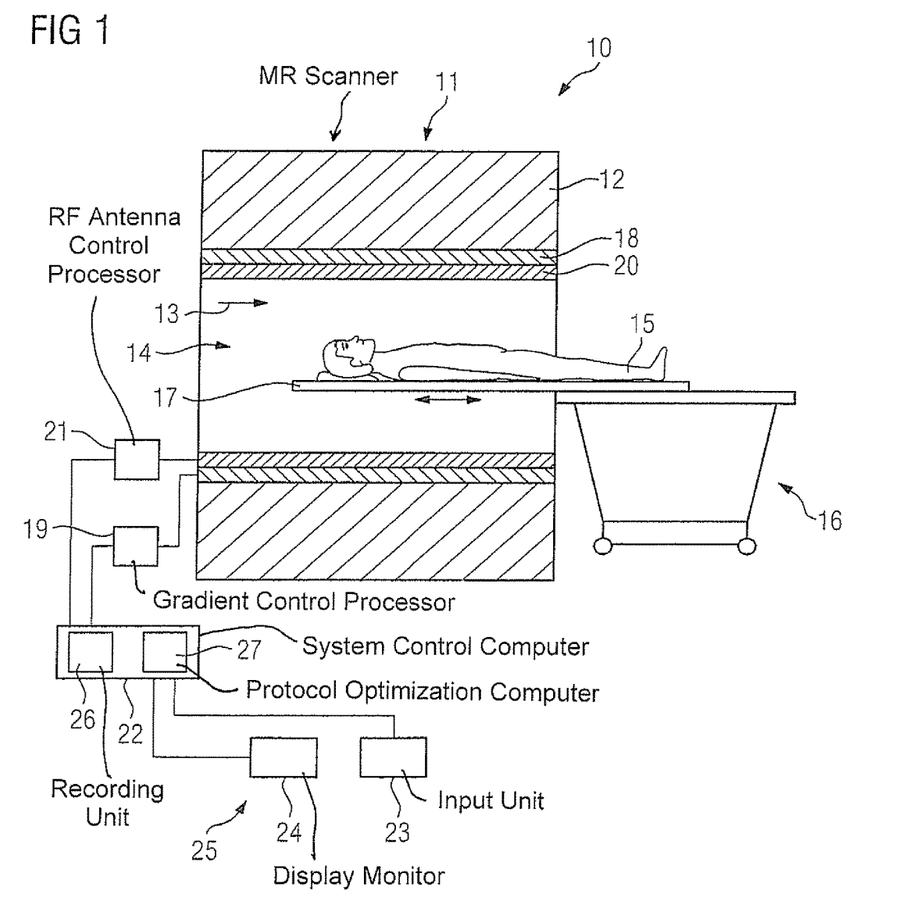
FIG. 1 shows a magnetic resonance apparatus according to the invention in a schematic representation.

FIG. 1 schematically illustrates a magnetic resonance apparatus 10. The magnetic resonance apparatus 10 has a scanner 11 having a superconducting basic field magnet 12 to generate a strong and constant basic magnetic field 13. The scanner 11 has a patient receiving area 14 for receiving a patient 15. In the exemplary embodiment, the patient receiving area 14 has a cylindrical shape and is surrounded in a circumferential direction by the scanner 11 in a cylindrical manner. Embodiments of the patient receiving area 14 deviating therefrom are also possible. The patient 15 can be moved into the patient receiving area 14 by a patient support 16 of the magnetic resonance apparatus 10. To this end, the patient support 16 has a patient table 17 that is movable within the patient receiving area 14.

The scanner 11 further has a gradient coil arrangement 18 for the generation of magnetic field gradients, which are used for spatial encoding during imaging. The gradient coil arrangement 18 is controlled by a gradient control processor 19 of the magnetic resonance apparatus 10. The scanner 11 further has a radio-frequency (RF) antenna 20 that is controlled by a radio-frequency antenna control processor 21 of the magnetic resonance apparatus 10 so as to radiate radio-frequency pulse sequences into an examination chamber substantially formed by the patient receiving area 14.

To control the basic field magnet 12, the gradient control processor 19 and the radio-frequency antenna control processor 21, the magnetic resonance apparatus 10 has a system control computer 22. The system control computer 22 controls the magnetic resonance apparatus 10 centrally, such as, for example, for the performance of a predetermined imaging gradient echo sequence. Moreover, the system control computer 22 can be configured to evaluate medical image data produced during the magnetic resonance examination.

The magnetic resonance apparatus 10 also has a user interface 25 connected to the system control computer 22. Control information such as imaging parameters and reconstructed magnetic resonance images can be displayed on a display monitor 24, composed to at least one monitor, of the user interface 25 for a medical operator. The user interface 25 also has an input unit 23 via which the medical operator can enter information and/or parameters during a measuring process.

Figure 2:
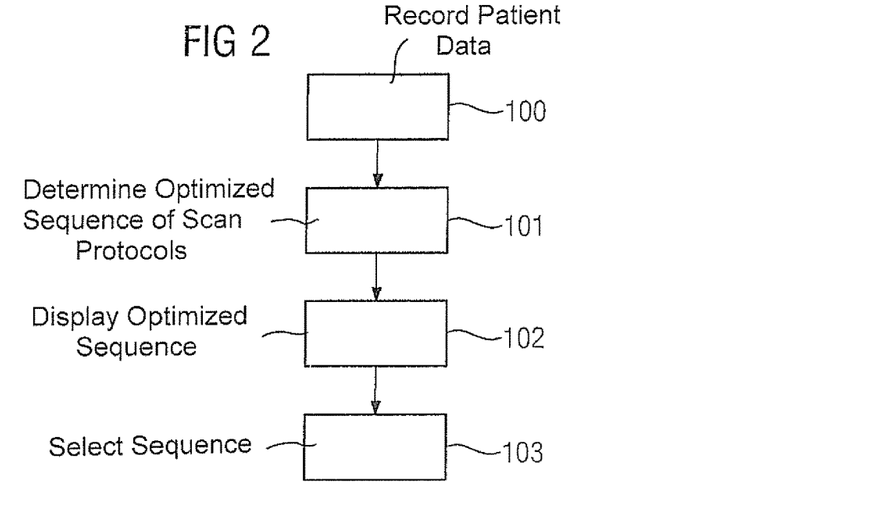
FIG. 2 is a schematic flowchart of the method according to the invention for the optimization of a sequence of two or more scan protocols for at least one magnetic resonance examination.

FIG. 2 shows a method according to the invention for the optimization of a sequence of two or more scan protocols for at least one magnetic resonance examination, wherein the at least one magnetic resonance examination is performed by the magnetic resonance apparatus 10. To this end, the control computer 22 has a recording unit 26 and a protocol optimization computer 27. The protocol optimization computer 27 and the recording unit 26 are designed for the execution of the method for the optimization of a sequence of two or more scan protocols for at least one magnetic resonance examination. For this purpose, the protocol optimization computer 27 and also the recording unit 26 includes software and/or computer programs stored in a memory of the system control computer 22 and are designed for the execution of the method for the optimization of a sequence of two or more scan protocols for at least one magnetic resonance examination by a processor unit of the system control computer 22.

In a first method step 100, patient data for a patient 15 are recorded by the recording unit 26 for an upcoming magnetic resonance examination. During the recording, the patient data of the patient 15 are acquired and the patient data used to selected a magnetic resonance examination or also a plurality of magnetic resonance examinations on the patient 15 and/or assign them to the patient 15. The magnetic resonance examination includes two or more different measurements, in particular magnetic resonance measurements, which each include at least one scan protocol and which should and/or must be executed for the selected and/or assigned magnetic resonance examination.

In this context, the acquisition and/or recording of the patient data can take place with reference to stored patient data and/or entered via an input, in particular a manual input by the medical operator, of the patient data. The recording unit 26 is arranged within the system control computer 22 and is connected to the user interface 25 and/or a patient database for the acquisition and/or recording of the patient data. The patient database can be stored in the memory of the system control computer 22 and/or be stored in an external memory. Moreover, the recording unit 26 has corresponding software and/or computer programs, stored in the memory of the system control computer 22.

For the majority of magnetic resonance examinations, a sequence of the individual different measurements is not mandatorily specified. Therefore, in this method step 100 the user, for example a doctor preparing the magnetic resonance examination, can already specify and/or select a desired and/or a preferred sequence of the two or more individual measurements of the magnetic resonance examination. Hence, the definition of a sequence of the two or more individual measurements also defines a sequence of the two or more scan protocols for the magnetic resonance examination.

In a further method step 101, an optimized sequence of the two or more scan protocols for the two or more different measurements of the magnetic resonance examination is determined. The optimized sequence of the two or more scan protocols is determined by the protocol optimization computer 27. For the optimization of the sequence of the two or more scan protocols, the protocol optimization computer 27 determines an expected heating for at least one component of the magnetic resonance apparatus 10 for at least one of the two or more measurements of the magnetic resonance examination. In the exemplary embodiment, the component of the magnetic resonance apparatus 10 includes the gradient coil arrangement 18 so that the expected heating is determined for at least one of the two or more measurements of the magnetic resonance examination for the gradient coil arrangement 18. In an alternative embodiment of the invention, the expected heating for at least one of the two or more measurements of the magnetic resonance examination can be determined for a further component or for two or more components of the magnetic resonance apparatus 10 in the further method step 101.

In this context, the expected heating of the at least one component, in particular the gradient coil arrangement 18, of the magnetic resonance apparatus 10 is, for example, only determined for one measurement or also two or more measurements out of the different measurements of the magnetic resonance examination by the protocol optimization computer 27. This can in particular be advantageous when the measurement, or also the two or more measurements, for which the expected heating is determined also include the energy-intensive measurements with high expected heating of the at least one component of the magnetic resonance apparatus 10. In this context, the expected heating is determined with reference to parameter settings, which are defined and/or can be defined within the individual scan protocols of the respective measurement of the magnetic resonance examination.

For the optimization of the sequence of the two or more scan protocols for the two or more different measurements of the magnetic resonance examination, the expected heating for the selected measurement or the two or more selected measurements is determined for all, whatever the type, sequences of the two or more scan protocols for the two or more different measurements of the magnetic resonance examination. In this context, the optimized sequence is determined as a function of a minimum expected heating of the at least one component, in particular the gradient coil arrangement 18, of the magnetic resonance apparatus 10 for the one measurement or for the two or more measurements out of the two or more different measurements of the magnetic resonance examination. In this context, the sequence of the two or more scan protocols selected as the optimized sequence is the one with which the expected heating of the at least one component, in particular the gradient coil arrangement 18, of the magnetic resonance apparatus 10 is minimal.

Moreover, in addition to the expected heating, the protocol optimization computer 27 can determine the available parameter space for the two or more individual measurements of the magnetic resonance examination. In this context, the available parameter space includes a setting range for setting parameters within the two or more scan protocols for the two or more different measurements of the magnetic resonance examination, wherein the parameters can be set by the user. The parameter space preferably includes a setting option for different measuring parameters, wherein the setting options for the different measuring parameters can be varied as a function of the sequence of the two or more scan protocols. The different measuring parameters can be, for example, an echo time (TE) or a relaxation time (TR) etc. The expected heating and the available parameter space are determined by the protocol optimization computer 27 for all possible sequences of the two or more scan protocols for the two or more different measurements of the magnetic resonance examination.

In this context, the optimization of the sequence of the two or more scan protocols for the two or more different measurements of the magnetic resonance examination can also be determined as a function of the expected heating and the available parameter space. In this context, the protocol optimization computer 27 can match the available parameter space and the minimum expected heating of the at least one component, in particular the gradient coil arrangement 18, of the magnetic resonance apparatus 10 to one another.

In an alternative embodiment of the invention, it is moreover conceivable for it to be possible that the optimization of the sequence of the two or more scan protocols for the two or more different measurements of the magnetic resonance examination is also determined as a function of a minimum expected overall heating for at least one component, in particular the gradient coil arrangement 18, of the magnetic resonance apparatus 10. In this context, the expected overall heating can be determined as a function of parameter settings, which are defined and/or can be defined within the individual scan protocols for the two or more different measurements of the magnetic resonance examination. Moreover, the expected overall heating for the at least one component, in particular for the gradient coil arrangement 18, of the magnetic resonance apparatus 10 can be determined for all of the two or more measurements of the magnetic resonance examination.

Moreover, in addition to the expected overall heating for the at least one component, in particular for the gradient coil arrangement 18, of the magnetic resonance apparatus 10, the protocol optimization computer 27 can additionally determine available parameter space for the two or more individual measurements of the magnetic resonance examination. The expected overall heating for the at least one component, in particular for the gradient coil arrangement 18, of the magnetic resonance apparatus 10 and the available parameter space can be determined by the protocol optimization computer 27 preferably for all possible sequences of the two or more scan protocols for the two or more different measurements of the magnetic resonance examination.

In this context, the optimization of the sequence of the two or more scan protocols for the two or more different measurements of the magnetic resonance examination can be determined as a function of a minimum expected overall heating of the at least one component, in particular the gradient coil arrangement 18, of the magnetic resonance apparatus 10. Moreover, the optimization of the sequence of the two or more scan protocols for the two or more different measurements of the magnetic resonance examination can also be determined as a function of the available parameter space. In this context, the protocol optimization computer 27 can match the available parameter space and the minimum expected overall heating of the at least one component, in particular the gradient coil arrangement 18, of the magnetic resonance apparatus 10 to one another.

In an alternative embodiment of the invention, the optimization of the sequence of the two or more scan protocols for the two or more different measurements of the magnetic resonance examination also only to be determined only as a function of a minimum expected heating for at least one of the two or more measurements of the magnetic resonance examination for the at least one component, in particular the gradient coil arrangement 18. Moreover, in another embodiment of the invention, the optimization of the sequence of the two or more scan protocols for the two or more different measurements of the magnetic resonance examination determined only as a function of an expected minimum overall heating of the at least one component, in particular the gradient coil arrangement 18, of the magnetic resonance apparatus 10 for the magnetic resonance examination.

In this further method step 101, the optimized sequence of the two or more scan protocols for the two or more different measurements of the magnetic resonance examination is determined as a function of at least one further magnetic resonance examination. Preferably, the further magnetic resonance examination and the magnetic resonance examination with the optimized sequence are arranged one after the other within a flowchart of the magnetic resonance apparatus 10.

In this context, the protocol optimization computer 27 the optimized sequence of the two or more scan protocols for the two or more different measurements of the magnetic resonance examination can be determined as a function of an heating status of the at least one component, in particular the gradient coil arrangement 18, of the magnetic resonance apparatus 10 before the start of the magnetic resonance examination. In this context, the expected heating status of the at least one component, in particular the gradient coil arrangement 18, of the magnetic resonance apparatus 10 at the start of the magnetic resonance examination is dependent on a sequence of the individual measurements and/or parameter setting of the further magnetic resonance examination, which is performed at an earlier time than the magnetic resonance examination with the optimized sequence. In this way, the sequence of the two or more scan protocols for the two or more different measurements of the magnetic resonance examination is advantageously optimized as a function of parameters and/or settings of further magnetic resonance examination and hence provides an advantageous protection, in particular against overheating, of individual components of the magnetic resonance apparatus 10.

In addition, in the further method step 101, the protocol optimization computer 27 can determine the optimized sequence of the two or more scan protocols for the two or more different measurements of the magnetic resonance examination as a function of an heating status of the at least one component, in particular the gradient coil arrangement 18, of the magnetic resonance apparatus 10 after the end of the magnetic resonance examination to be optimized. This enables the expected heating status of the at least one component to be taken into account by the protocol optimization computer 27 for the optimization of a further magnetic resonance examination following the magnetic resonance examination in a flowchart.

In addition, in the further method step 101, the protocol optimization computer 27 can determine the optimized sequence of the two or more scan protocols for the two or more different measurements of the magnetic resonance examination as a function of an heating status of the at least one component, in particular the gradient coil arrangement 18, of the magnetic resonance apparatus 10 of a further magnetic resonance examination, which follows the magnetic resonance examination in a flowchart. This enables, for example, the optimization of not only one single magnetic resonance examination with respect to a sequence of the two or more scan protocols for the two or more different measurements but also the optimization of the sequence of a plurality of magnetic resonance examinations as a function of the respective sequences of the two or more scan protocols for the two or more different measurements for the respective magnetic resonance examination.

Following the determination of the optimized sequence of the two or more scan protocols for the two or more different measurements of the magnetic resonance examination, in a further method step 102, the optimized sequence of the two or more scan protocols is displayed by the display monitor 24 of the magnetic resonance apparatus 10. In addition to the optimized sequence, the user is also shown the further, non-optimized sequences of the two or more scan protocols for the two or more different measurements of the magnetic resonance examination. The user can use this display to select a sequence. In this context, the user can select both the optimized sequence of the two or more scan protocols and a further, non-optimized sequence of the two or more scan protocols. The selected sequence of the two or more scan protocols is used to perform the magnetic resonance examination.

To assist in the selection of the sequence of the two or more scan protocols, in addition to each sequence of the two or more scan protocols shown, a piece of optimization information is determined and displayed together with the sequence of the two or more scan protocols. In this context, the optimization information is calculated by the protocol optimization computer 27 within the further method step 101. In this context, the optimization information includes a utilization factor for at least one component, in particular the gradient coil arrangement 18, of the magnetic resonance apparatus 10. In addition, the optimization information can also include a value for a deviation from the optimized sequence of the two or more scan protocols for the selected sequence of the two or more scan protocols.

In the further method step 102, the optimization information for the respective sequence of the two or more scan protocols is displayed. In this context, the optimization information can be displayed differently as a function of a value for a deviation from the optimized sequence of the two or more scan protocols for the different sequences of the two or more scan protocols. Particularly advantageously, suitable to this end is a "traffic light," with which, for example, a green color shade signals a slight deviation of the selected sequence of the two or more scan protocols from the optimized sequence of the two or more scan protocols to the user. On the other hand, a red color shade can signal a high deviation of the selected sequence of the two or more scan protocols from the optimized sequence of the two or more scan protocols to the user.

In addition to the display of the optimized sequence and the further sequences, the user is also in each case shown the available parameter space. This enables the user also to select the selection of the sequence with reference to the available parameter space for the individual measuring parameters.

Subsequently thereto, in a further method step 103, a sequence of the two or more scan protocols is selected, wherein the selection is performed manually by the user.

Figure 3:
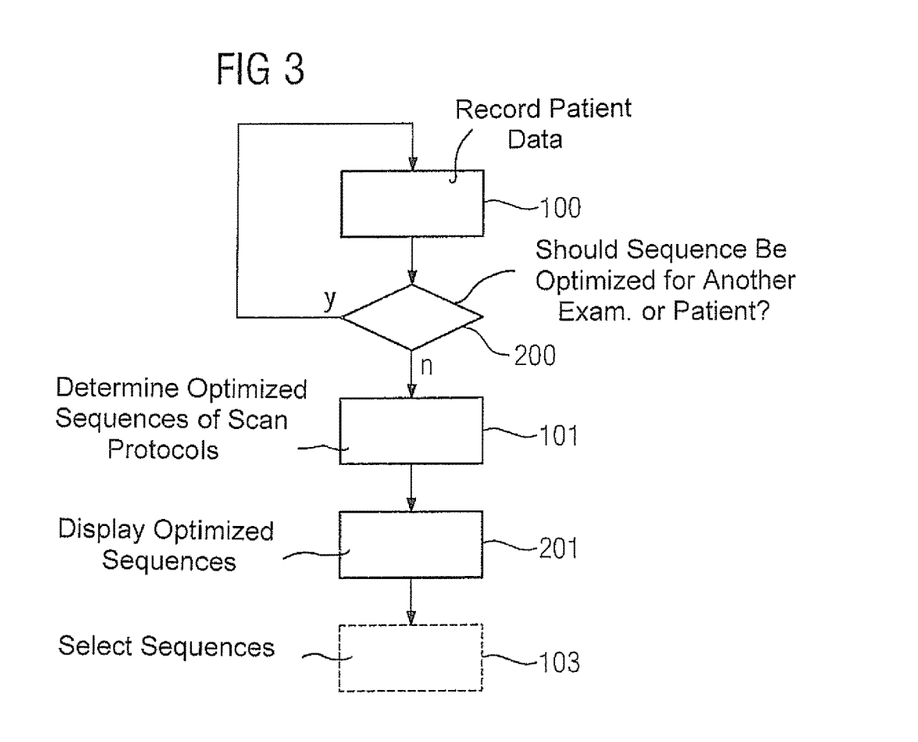
FIG. 3 is a schematic flowchart of the method according to the invention for a number of magnetic resonance examinations.

FIG. 3 shows a further course of the method according to the invention, wherein here an optimized sequence of two or more scan protocols are compiled for a plurality of, in particular two or more, magnetic resonance examinations, such as is advantageous in particular when planning two or more magnetic resonance examinations by means of the magnetic resonance apparatus 10 for a whole day. Substantially identical features and features are generally given the same reference numbers. The following description is substantially restricted to the differences from the exemplary embodiment in FIG. 2, wherein reference is made to the description of the exemplary embodiment in FIG. 2 with respect to identical features and functions.

In this method shown in FIG. 3 for the optimization of a sequence of two or more scan protocols, initially, the method step 100 for the recording of patient data for at least one patient 17 is carried out for a first magnetic resonance examination. The method step 100 corresponds to the method step 100 of the method for the optimization of a sequence of two or more scan protocols for the magnetic resonance examination in FIG. 2.

Following the method step 100 for the recording of patient data for at least one patient 17, in a further method step 200, the question is asked as to whether it is necessary to optimize a sequence of two or more scan protocols for a further magnetic resonance examination and/or whether a further patient 17 is to be examined. If this question is answered YES, the method step 100 is restarted and initially a recording of patient data of a patient 17 for the further magnetic resonance examination also takes place. The question can be answered by the user and/or automatically, for example if there is a ready compiled flowchart in which it is already specified which magnetic resonance examinations are to be performed and/or which patients are to be examined.

If, in the method step 200, the question is answered NO, this is followed by the further method step 101 for the determination of an optimized sequence of the two or more scan protocols for the two or more different measurements for the magnetic resonance examinations such as is described in FIG. 2. In this context, during the optimization of the sequence of the two or more scan protocols for the two or more different measurements for each of the magnetic resonance examinations, an optimized sequence of the two or more scan protocols for the two or more different measurements of the further magnetic resonance examinations is taken into account.

Following this, in a further method step 201 the optimized sequences of the two or more scan protocols for the two or more different measurements for the two or more different magnetic resonance examinations are shown or displayed. The method step 102 for the display takes place similarly to the method step for the display in the description of FIG. 2, wherein both an optimized sequence of the two or more measurements of the individual magnetic resonance examinations is displayed and an optimized sequence of the individual magnetic resonance examinations with respect to one another. Moreover, following the method step 201, it is optionally possible for the further method step 103 to be performed in that a user is able to define and/or select a selection of an optimized sequence. In this context, the user can both define and/or select the sequence of the individual magnetic resonance examinations and a sequence of the two or more scan protocols for the two or more different measurements for the individual magnetic resonance examinations.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a magnetic resonance (MR) data acquisition scanner comprising:
    in a computer, defining first control parameters of a first scan protocol that set operation of an MR data acquisition scanner in order to acquire first MR data that are sufficient for a first MR image to be reconstructed from said first MR data;
    in said control computer, also defining second control parameters of a second scan protocol that set operation of the MR data acquisition scanner in order to acquire second MR data that are sufficient for a second MR image to be reconstructed from said second MR data;
    in said computer, optimizing a sequence for execution of said first and second scan protocols by said MR data acquisition scanner according to different optimization criteria so as to produce an optimized sequence for each of said different optimization criteria, each optimized sequence specifying an order in which said first and second scan protocols are to be performed relative to each other;
    at a display screen in communication with said computer, displaying each of said optimized sequences for viewing by a user;
    receiving a manual input into said computer made by the user that selects one of the optimized sequences, as a selected optimized sequence;
    from said computer, providing control signals to said MR data acquisition scanner representing the control parameters of the first and second scan protocols so as to execute an MR examination comprising the first and second scan protocols in an order corresponding to the selected optimization sequence, and thereby operating the MR data acquisition scanner to acquire said first MR data and said second MR data in said order; and
    making the first MR data and the second MR data available from the computer as respective data files in a form allowing reconstruction of said first MR image and said second MR image respectively from said data files.

2. A method as claimed in claim 1 wherein said MR data acquisition scanner comprises a gradient coil arrangement that is operated in said first and second scan protocols in order to generate gradient fields having a gradient strength and with a slew rate, and comprising, in said computer, determining at least one of said optimized sequences by executing an estimation algorithm to estimate heating of said gradient coil arrangement dependent on the gradient strength and the slew rate, and using the estimated heating of said gradient coil arrangement as the optimization criterion for said at least one of said optimized sequences.

3. A method as claimed in claim 2 comprising determining, in said computer, an available parameter space for implementing said magnetic resonance examination dependent on said estimated heating of said gradient coil arrangement.

4. A method as claimed in claim 3 comprising using said available parameter space, to determine one of said optimized sequences of said multiple scan protocols.

5. A method as claimed in claim 1 wherein said first scan protocol is a scan protocol for implementing a diffusion measurement, and said second scan protocol is a scan protocol for implementing a time of flight measurement.

6. A method as claimed in claim 1 comprising operating said MR data acquisition scanner from said computer to execute at least one further MR examination, in addition to said magnetic resonance examination, and optimizing said sequence of said multiple scan protocols for said MR examinations dependent on said at least one further MR examination.

7. A method as claimed in claim 1 comprising providing said computer with an electronic designation of a heating status of at least one component of said magnetic resonance imaging data scanner before starting said MR examination, and determining one of said optimized sequences of said multiple scan protocols dependent on said heating status.

8. A method as claimed in claim 7 comprising determining said heating status of said at least one component of said magnetic resonance imaging data acquisition scanner after an end of said MR examination.

9. A method as claimed in claim 1 comprising also displaying at least one item of optimization information, generated by said computer, at said display screen together with the display of each of said optimized sequences.

10. A method as claimed in claim 9 comprising generating said at least one item of optimization information as at least one of a utilization factor of said MR data acquisition scanner, and a value representing a deviation from the respective optimized sequence displayed therewith.

11. A method as claimed in claim 9 comprising generating said at least one item of optimization information as a value for a deviation from said respective optimized sequence, and also displaying said respective optimized sequence at said display screen with said deviation.

12. A magnetic resonance (MR) apparatus comprising:
an MR data acquisition scanner;
a computer configured to define first control parameters of a first scan protocol that set operation of an MR data acquisition scanner in order to acquire first MR data that are sufficient for a first MR image to be reconstructed from said first MR data;
said control computer being configured to also define second control parameters of a second scan protocol that set operation of the MR data acquisition scanner in order to acquire second MR data that are sufficient for a second MR image to be reconstructed from said second MR data;
said computer being configured to optimize a sequence for execution of said first and second scan protocols by said MR data acquisition scanner according to different optimization criteria so as to produce an optimized sequence for each of said different optimization criteria, each optimized sequence specifying an order in which said first and second scan protocols are to be performed relative to each other;
said computer being configured to display, at a display screen in communication with said computer, each of said optimized sequences for viewing by a user;
said computer being configured to receive a manual input made by the user that selects one of the optimized sequences, as a selected optimized sequence;
said computer being configured to provide control signals to said MR data acquisition scanner representing the control parameters of the first and second scan protocols so as to execute an MR examination comprising the first and second scan protocols in an order corresponding to the selected optimization sequence, and thereby operate the MR data acquisition scanner to acquire said first MR data and said second MR data in said order; and
said computer being configured to make the first MR data and the second MR data available from the computer as respective data files in a form allowing reconstruction of said first MR image and said second MR image respectively from said data files.

13. A non-transitory, computer-readable data storage medium encoded with programming instructions, said storage medium being loaded into a computer of a magnetic resonance (MR) apparatus comprising an MR data acquisition scanner, said programming instructions causing said computer to:
define first control parameters of a first scan protocol that set operation of an MR data acquisition scanner in order to acquire first MR data that are sufficient for a first MR image to be reconstructed from said first MR data;
also define second control parameters of a second scan protocol that set operation of the MR data acquisition scanner in order to acquire second MR data that are sufficient for a second MR image to be reconstructed from said second MR data;
optimize a sequence for execution of said first and second scan protocols by said MR data acquisition scanner according to different optimization criteria so as to produce an optimized sequence for each of said different optimization criteria, each optimized sequence specifying an order in which said first and second scan protocols are to be performed relative to each other;
at a display screen in communication with said computer, displaying each of said optimized sequences for viewing by a user;
receive a manual input into said computer made by the user that selects one of the optimized sequences, as a selected optimized sequence;
provide control signals to said MR data acquisition scanner representing the control parameters of the first and second scan protocols so as to execute an MR examination comprising the first and second scan protocols in an order corresponding to the selected optimization sequence, and thereby operate the MR data acquisition scanner to acquire said first MR data and said second MR data in said order; and
make the first MR data and the second MR data available from the computer as respective data files in a form allowing reconstruction of said first MR image and said second MR image respectively from said data files.

* * * * *